United States Patent [19]

Wei et al.

[11] Patent Number: 5,300,274
[45] Date of Patent: Apr. 5, 1994

[54] METHOD FOR MAKING MOLYBDENUM AND SULFUR CONTAINING COMPOUNDS

[75] Inventors: Liwen Wei, Somerville; Catherine L. Coyle, Mendham, both of N.J.; Thomas R. Halbert, Baton Rouge, La.; Edward I. Stiefel, Bridgewater, N.J.

[73] Assignee: Exxon Research and Engineering Company, Florham Park, N.J.

[21] Appl. No.: 603,064

[22] Filed: Oct. 25, 1990

[51] Int. Cl.$^5$ .............................. C01G 39/06
[52] U.S. Cl. ............................ 423/511; 423/53; 423/56; 423/DIG. 14; 502/220
[58] Field of Search ............ 423/DIG. 14, 53, 56, 423/57, 511, 560; 502/220

[56] References Cited

U.S. PATENT DOCUMENTS

| | | | |
|---|---|---|---|
| 3,860,419 | 1/1975 | Weber | 75/103 |
| 3,965,041 | 6/1976 | van Klinken | 252/437 |
| 4,430,442 | 2/1984 | Sawyer | 502/220 |

OTHER PUBLICATIONS

"Synthesis, Interconversions, & Structural Characterization of the [(S$_4$)2MOS]$^{2-}$, [(Mo$_2$S$_{10}$)$^{2-}$] and [(Mo$_2$S$_{12}$)$^{2-}$] Anions" M. Graganjac et al. *Inorg. Chem.* 1982, 21, 3321-3332.

"(NH$_4$)$_2$ [(S$_2$)$_2$Mo(S$_2$)$_2$Mo(S$_2$)$_2$].2H$_2$O, A Novel Sulfur-Rich Coordination Compound With Two Nonequivalent Complex Anions Having the Same Point Group but Different Structures: Crystal & Molecular Structures" A. Müller et al. *Inorg. Chem.*, 1980, 19, 2835-2836.

"[(S$_2$)$_2$Mo(S$_2$)$_2$Mo(S$_2$)$_2$]$^{2-}$, A Novel Complex Containing Only S$_{22-}$ Ligand and a Mo-Mo Bond" A. Müller et al. *Angew. Chem. Int. Engl.* vol. 17, p. 279 (1978).

Primary Examiner—Gary P. Straub
Assistant Examiner—Timothy C. Vanoy
Attorney, Agent, or Firm—Joseph J. Dvorak

[57] ABSTRACT

A method for preparing molybdenum and sulfur containing compounds of the general formula $X_2Mo_2S_{1-2}.yH_2O$, where X is a cation selected from the group consisting of $Na^+$, $K^+$, $R_4N^+$, $R_3NH^+$, $R_2NH_2^+$, $RNH_3^+$, $NH_4^+$, $R_4P^+$, $R_4As^+$, $(R_3P)_2N^+$, R is a $C_1$-$C_{30}$ alkyl, $C_6$-$C_{30}$ aryl, $C_7$-$C_{30}$ aralkyl or $C_2$-$C_{30}$ alkoxyalkyl group and mixtures thereof, and y is from 0 to 2. The method comprises preparing a sulfide solution that contains from about 9 wt. % to about 13 wt. % sulfide sulfur; contacting the solution with elemental sulfur and a hydroxide; adding a molybdenum compound for a time and at a temperature sufficient to form a reaction mixture and a precipitate; separating the precipitate; and contacting the remaining reaction mixture with additional sulfide solution to form $(NH_4)_2Mo_2S_{12}.yH_2O$. When compounds containing cations other than $NH_4^+$ are to be produced, the $(NH_4)_2Mo_2S_{12}.yH_2O$ is contacted with a cation exchange compound containing a desired substitute cation selected from above and an anion selected from the group consisting of $Cl^-$, $Br^-$, $F^-$, $I^-$, $BF_4^-$, $PF_6^-$, $OH^-$, $BR_4^-$ where R is a $C_1$-$C_{30}$ alkyl, $C_6$-$C_{30}$ aryl, $C_7$-$C_{30}$ aralkyl or $C_2$-$C_{30}$ alkoxyalkyl group, and mixtures thereof, in the presence of a solvent and for a time and at a temperature sufficient to form $X_2Mo_2S_{1-2}.yH_2O$, where X is other than $NH_4^+$.

9 Claims, No Drawings

METHOD FOR MAKING MOLYBDENUM AND SULFUR CONTAINING COMPOUNDS

FIELD OF THE INVENTION

The invention relates to the synthesis of compounds containing molybdenum and sulfur. More particularly, the invention relates to the synthesis of molybdenum compounds containing an $Mo_2S_{12}^{2-}$ anion.

BACKGROUND OF THE INVENTION

Commercial transition metal sulfide (TMS) catalysts and enzymes containing TMS sites have caused researchers to focus attention on the coordination chemistry of sulfido-molybdenum complexes. Efforts to develop mononuclear, polynuclear, and heteronuclear Mo-S complexes which serve as structural or reactivity models for molybdenum-sulfido catalytic systems have led to the synthesis of several molybdenum complexes. However, efforts to produce these complexes are significantly restricted by the lack of appropriate Mo-S starting materials.

Hydrated salts containing $Mo_2S_{12}^{2-}$ as an anion were first prepared as ammonium salts. A. Muller, W. Nolte, and B. Krebs, "$[S_2)_2 Mo(S_2)_2 Mo(S_2)_2^{2-}$, a Novel Complex Containing Only $S_2^{2-}$ Ligands and a Mo-Mo Bond", *Angew. Chem. Int. Engl.*, Vol. 17, p. 279 (1978) discuss preparing $Mo_2S_{12}^{2-}$ anion-containing salts. The method involves heating an ammonium sulfide solution with $(NH_4)_2MoO_4$, separating the mixture, and cooling and diluting the filtrate. During the reaction, $Mo_3S_{13}^{2-}$ anions are also formed. In addition, the synthesis led to variable yields of the desired ammonium salt, $(NH_4)_2Mo_2S_{12}\cdot 2H_2O$. Salts containing the $Mo_2S_{12}^{-2}$ anion and a cation other than ammonium ($NH_4^+$) were unknown.

M. Draganjac, et al., "Synthesis, Interconversions and Structural Characterization of the $[(S_4)_2Mo_2S_{10}]^{2-}$, $(Mo_2S_{10})^{2-}$ and $(Mo_2S_{12})^{2-}$ Anions", *Inorg. Chem.*, Vol. 21, pp. 3321-3332 (1982) discuss the preparation of $(Ph_4P)_2Mo_2S_{10.56}$, a mixture of $(Ph_4P)_2Mo_2S_{10}$ and $(Ph_4P)_2Mo_2S_{12}$, by reacting $(Ph_4P)_2MoS_4$ with dibenzyltrisulfide in dimethylformamide (DMF). Ethanol and ether were then added and dark red crystals resulted which were washed with ethanol and ether. A 58% yield of $(Ph_4P)_2Mo_2S_{10.56}$ was obtained.

S. A. Cohen, et al., "Dinuclear Tungsten (V) and Molybdenum (V) Compounds Containing $M_2S_2(\mu$-$S)_2^{2+}$ Cores: Synthesis and Reactivity of $[N(C_2H_5)_4]_2M_2S_{12}$ (M=W or Mo) and the Crystal Structure of $[N(C_2H_5)_4]_2W_2S_2(\mu$-$S)_2(S_4)_2$", *Inorg. Chem.*, Vol. 24, p. 4657 (1985) teaches preparing salts containing $Mo_2S_{12}^{2-}$ anions by reacting elemental sulfur and $(NH_4)_2MoS_4$ in DMF and heating. A red-black solution is formed and tetraethylammonium bromide is then added and the DMF is removed at 65° C. under vacuum. The solids are extracted with acetonitrile to form a filtrate and a salt containing an $Mo_2S_{12}^{2-}$ anion is recrystallized from the filtrate. A 62% yield of the salt was obtained.

Although capable of producing compounds containing $Mo_2S_{12}^{2-}$ anions, the reaction schemes in the prior art suffer from numerous drawbacks. These drawbacks include: low yields of $Mo_2S_{12}^{2-}$ anion containing compounds; low $Mo_2S_{12}^{2-}$ anion purity; the production of dimethylammonium bromide, a skin and mucous membrane irritant; the need to bubble $H_2S$ gas into solution to produce $Mo_2S_{12}^{2-}$ anions; and difficulty in controlling the concentration of the sulfide sulfur reactant. As a result, the prior art preparations are not suitable for large scale production of pure compounds containing the $Mo_2S_{12}^{2-}$ anion.

It is therefore an object of the invention to provide a method for producing, in relatively high yield, molybdenum and sulfur containing compounds in pure form that have $Mo_2S_{12}^{2-}$ as the anion.

Another object of the invention is to provide a method for producing molybdenum and sulfur containing compounds that have $Mo_2S_{12}^{2-}$ as the anion that provides a means for controlling the sulfide sulfur concentration of the reaction.

Other objects of the invention will become more apparent to those skilled in the art upon reading the following description in conjunction with the examples, provided for illustrative purposes.

SUMMARY OF THE INVENTION

The invention is a method for preparing compounds containing molybdenum and sulfur having the general formula $X_2Mo_2S_{12}\cdot yH_2O$, where X is a cation selected from the group consisting of $Na^+$, $K^+$, $R_4N^+$, $R_3NH^+$, $R_2NH_2^+$, $RNH_3^+$, $NH_4^+$, $R_4P^+$, $R_4As^+$, $(R_3P)_2N^+$ and mixtures thereof where R is a $C_1$-$C_{30}$ alkyl, $C_6$-$C_{30}$ aryl, $C_7$-$C_{30}$ aralkyl or $C_2$-$C_{30}$ alkoxyalkyl group and where y is from 0 to 2 comprising:

(a) preparing a sulfide solution containing from about 9 wt. % to about 13 wt. % sulfide sulfur;

(b) contacting the sulfide solution with elemental sulfur and a hydroxide to form a polysulfide solution;

(c) adding a molybdenum compound to the polysulfide for a time and under conditions sufficient to form a reaction mixture and a precipitate;

(d) separating the precipitate from the reaction mixture;

(e) contacting the reaction mixture with additional sulfide solution in an amount sufficient to form $(NH_4)_2Mo_2S_{12}\cdot yH_2O$; and, (f) when X is to be other than $NH_4^+$, the $(NH_4)_2Mo_2S_{12}\cdot yH_2O$ crystals are separated, dried and then contacted with a compound containing a cation selected from the group consisting of $Na^+$, $K^+$, $R_4N^+$, $R_3NH^+$, $R_2NH_2^+$, $RNH_3^+$, $NH_4^+$, $R_4P^+$, $R_4As^+$, $(R_3P)_2N^+$ and mixtures thereof and where R is a $C_1$-$C_{30}$ alkyl, $C_6$-$C_{30}$ aryl, $C_7$-$C_{30}$ aralkyl or $C_2$-$C_{30}$ alkoxyalkyl group, in the presence of solvent and for a time sufficient to form a precipitate of the general formula $X_2Mo_2S_{12}\cdot yH_2O$, where X is other than $NH_4^+$.

In another aspect of the invention step (a) includes preparing a sulfide solution by diluting a commercial sulfide solution containing greater than 13 wt. % sulfide sulfur with an appropriate amount of water until the sulfide sulfur of the solution ranges from about 9 wt. % to about 13 wt. %.

DETAILED DESCRIPTION

Compounds containing $Mo_2S_{12}^{2-}$ anions are important precursors to molybdenum sulfide hydrogenation catalysts. The invention involves preparing a polysulfide solution comprised of a sulfide solution, elemental sulfur and hydroxide and reacting the polysulfide solution with a molybdenum compound.

The term "polysulfide" is defined herein as a series of complex divalent negative sulfide ions, $(S_x^{2-})$, formed by contacting a sulfide source, with elemental sulfur and a hydroxide in the presence of water. The most preferred sulfide source is ammonium sulfide, however, other types of sulfide sources may be used such as, an alkaline metal sulfide of either sodium or potassium. The elemental sulfur added to the sulfide source complexes with the sulfide source to form these complex divalent negative sulfide ions. Elemental sulfur exists in rhombic, monoclinic and amorphous sulfur form and may be derived from a number of conventional sources. The hydroxide includes ammonium hydroxide and alkali metal hydroxides such as sodium and potassium hydroxide, however, most preferred is ammonium hydroxide.

The sulfide sulfur concentration of the sulfide solution is essential to the preparation of compounds containing the $Mo_2S_{12}^{2-}$ anion under the method of the present invention. Sulfide solutions that have from about 9 wt. % to about 13 wt. % sulfide sulfur are the most preferred. It has been found that sulfide solutions containing from about 19 wt. % to about 25 wt. % sulfide sulfur do not produce pure $(NH_4)_2Mo_2S_{12}\cdot yH_2O$ crystals in sufficient yield for commercial exploitation and contribute to the production of compounds containing various other Mo-S anions. Normally, the sulfide sulfur concentration of a sulfide solution is determined by iodometric titration and reported as the percent $(NH_4)_2S$. However, since all of the sulfide sulfur may not be present as $(NH_4)_2S$ the weight percent sulfide sulfur is determined herein by direct chemical analysis.

Commercial sulfide solutions may be used, however, the sulfide sulfur concentration of these solutions will vary depending on the commercial supplier. These solutions must therefore be adjusted to fall within the range of from about 9 wt. % to about 13 wt. %. In order to make these adjustments the sulfide solution is diluted with the required amount of water until the desired weight percent sulfide sulfur in solution is obtained.

Sulfide solutions, such as aqueous ammonium sulfide, may be prepared in the laboratory by bubbling $H_2S$ through a solution of a concentrated hydroxide, such as $NH_4OH$ (14.8N), at ambient temperatures and atmospheric pressure. However, as with some commercial sulfide solutions the sulfide sulfur concentration that results is greater than 13 wt. % and in some cases is 19 wt. % or greater. The commercial sulfide solution must then be diluted with water so that the sulfide sulfur concentration is adjusted to be in the desired range.

Other methods of preparing suitable sulfide solutions may exist and these may also be used in connection with the present invention.

Having prepared the sulfide solution the next step involves contacting the sulfide solution with a specified amount of elemental sulfur and a hydroxide to form the polysulfide solution. Next the polysulfide is reacted with a molybdenum compound and the combined polysulfide solution and molybdenum compound is stirred for several hours and forms a reaction mixture and a precipitate.

The molybdenum compound employed must be reactive with the polysulfide solution. Molybdenum compounds that have a hexavalent Mo bound by oxygen are most preferred. These molybdenum compounds are selected from the group consisting of molybdic acid, molybdate and molybdenum trioxide; preferred are ammonium molybdate and molybdenum trioxide; and most preferred is ammonium molybdate.

In order to maximize the yield of molybdenum and sulfur compounds containing pure $Mo_2S_{12}^{2-}$ anions, it is preferred that the sulfide solution, elemental sulfur, hydroxide and molybdenum compounds be formulated in a fixed ratio amount. A preferred ratio is shown below.

| | |
|---|---|
| Ammonium Sulfide Solution (ml) | 10 |
| (9 wt. % to 13 wt. % sulfide sulfur) | |
| Elemental Sulfur (g) | 4 |
| Concentrated Hydroxide (ml) | 5 |
| (ammonium hydroxide) | |
| Molybdenum Compound (g) | 1 |
| $(NH_4)_6Mo_7O_{24}\cdot 4H_2O$ ammonium molybdate) | |
| Additional Ammonium Sulfide (ml) | 20 |
| (9 wt. % to 13 wt. % sulfide sulfur) | |

A precipitate forms in the reaction mixture after the addition of the first four reagents and is later separated from the reaction mixture and discarded. The separation may be accomplished by any number of conventional techniques. For example, the reaction mixture, containing the precipitate, may be mechanically separated by centrifugation or passed through porous filters sized to impede the passage of the precipitate particles.

The reaction mixture is then contacted with the additional sulfide solution containing from about 9 wt. % to about 13 wt. % sulfide sulfur in the ratio shown above to form $(NH_4)_2Mo_2S_{12}\cdot yH_2O$ crystals. These crystals begin to appear about 30 minutes to about 120 minutes after the reaction mixture is contacted with the sulfide. Once formed, the crystalline product is separated and washed with a solvent in a manner similar to that previously described.

Solvents suitable for use in the invention must be capable of solubilizing all of the reagents without altering the amount of available sulfide sulfur and include organic solvents such as alcohol, ether, acetonitrile, inorganic solvents, such as water, and mixtures thereof; most preferred is water.

The cation, X, of the crystalline product is $NH_4^+$, but compounds containing cations other than $NH_4^+$ may be obtained by a cation exchange reaction. The cation exchange reactions involve reacting $(NH_4)_2Mo_2S_{12}$ crystals, with compounds containing the desirable cation and an anion. The cation exchange is carried out in the presence of a solvent and a precipitate forms. The precipitate is a compound having the general formula $X_2Mo_2S_{12}\cdot yH_2O$, where X is the desired cation substitute.

The cation of the cation exchange compound is selected from the group consisting of $Na^+$, $K^+$, $R_4N^+$, $R_3NH^+$, $R_2NH_2^+$, $RNH_3^+$, $R_4P^+$, $R_4As^+$, $(R_3P)_2N^+$ where R is a $C_1$–$C_{30}$ alkyl, $C_6$–$C_{30}$ aryl, $C_7$–$C_{30}$ aralkyl or $C_2$–$C_{30}$ alkoxyalkyl group, and mixtures thereof. Preferred R groups include ethyl, propyl, butyl, benzyl, and phenyl.

The anion of the cation exchange compound is selected from the group consisting of $Cl^-$, $Br^-$, $F^-$, $I^-$, $BF_4^-$, $PF_6^-$, $OH^-$, $BR_4^-$ where R is a $C_1$–$C_{30}$ alkyl, $C_6$–$C_{30}$ aryl, $C_7$–$C_{30}$ aralkyl or $C_2$–$C_{30}$ alkoxyalkyl group, and mixtures thereof.

The method is carried out at temperatures ranging from the higher of the melting point of the precipitate in the reaction mixture or the reflux temperature of the reaction mixture to as low as 0° C. and more preferably is carried out from about 15° C. to about 100° C. and most preferably is carried out at room temperature (25° C.). The pressure is preferably atmospheric pressure, although higher or lower pressures may be used.

The invention may be further understood by reference to the following examples which are included for illustrative purposes and are not intended to limit the scope of the invention in any way.

Example 1

Synthesis of $(NH_4)_2Mo_2S_{12}.2H_2O$

Ammonium molybdate (20 g) is added at room temperature to 200 ml of an aqueous ammonium sulfide solution containing about 9 wt. % to about 13 wt. % sulfide sulfur, elemental sulfur (80 g) and concentrated ammonium hydroxide (100 ml). The resulting mixture was stirred for 24 hours until a precipitate formed and was filtered. The precipitate was discarded and the filtrate obtained was diluted with 400 ml of additional aqueous ammonium sulfide solution containing about 9 wt. % to about 13 wt. % sulfide sulfur. Black crystals formed in the above solution in 1 hour to 2 hours. The mixture was then filtered, washed with $H_2O$, ethanol, $CS_2$, ether and dried to give 34 g of the black solid, $(NH_4)_2Mo_2S_{12}.2H_2O$, in 92% yield based on molybdenum. Chemical analysis of the $(NH_4)_2Mo_2S_{12}.2H_2O$ product gave the following results:

| Component | Wt. % Theoretical | Wt. % Actual |
| --- | --- | --- |
| Mo | 29.58% | 28.86% |
| S | 59.30% | 62.43% |
| N | 4.32% | 4.25% |

Example 2

Synthesis of $(NH_4)_2Mo_2S_{12}.2H_2O$

Ammonium molybdate (30 g) was added at room temperature to 150 ml of an aqueous ammonium sulfide solution containing 19% sulfide sulfur, water (150 ml), elemental sulfur (120 g) and concentrated ammonium hydroxide (150 ml). Since the sulfide sulfur content of the solution is about 19 wt. % which is outside of the desired range, the solution was first diluted with 150 ml water so that the final sulfide sulfur concentration was about 9.5 wt. %. The resulting mixture was stirred for 24 hours and filtered. The precipitate was discarded and the filtrate was diluted with an ammonium sulfide solution prepared by diluting an additional 300 ml of ammonium sulfide solution, containing 19% sulfide sulfur, with 300 ml water. Black crystals grew from the above solution in 1 to 2 hours. The mixture was then filtered, washed with $H_2O$, ethanol, $CS_2$, ether and dried to give approximately 34 g of the black solid, $(NH_4)_2Mo_2S_{12}.2H_2O$, in approximately 92% yield based on molybdenum.

Example 3

Synthesis of $[(Bu_4N)_2Mo_2S_{12}].2H_2O$ by Cation Exchange

Excess tetrabutylammonium chloride was added to methanol (60 ml) saturated with the $(NH_4)_2Mo_2S_{12}.2H_2O$ salt prepared in Example 1. Black crystals rapidly formed and were filtered and washed with ether and air dried to give 500 mg of $[(Bu_4N)_2Mo_2S_{12}].2H_2O$.

Although particular embodiments of the invention have been shown and described, it is to be understood that the scope of the invention is not limited to these embodiments, since modifications can be made by one of ordinary skill in the art.

What is claimed is:

1. A method for preparing molybdenum and sulfur containing compounds of the general formula $X_2Mo_2S_{12}.yH_2O$, where X is a cation selected from the group consisting of $Na+$, $K+$, $R_4N+$, $R_3NH+$, $R_2NH_2+$, $RNH_3+$, $NH_4+$, $R_4P+$, $R_4As+$, $(R_3P)_2N+$, R is a $C_1$-$C_{30}$ alkyl, $C_6$-$C_{30}$ aryl, $C_7$-$C_{30}$ aralkyl or $C_2$-$C_{30}$ alkoxyalkyl group, and mixtures thereof, and y is from 0 to 2, comprising:

(a) preparing an ammonium sulfide solution containing from about 9 wt. % to about 13 wt. % sulfur;

(b) contacting the sulfide solution of step (a) with an appropriate amount of elemental sulfur and a hydroxide to form a polysulfide solution;

(c) adding a molybdenum compound selected from the group consisting of molybdic acid, a molybdate and molybdenum trioxide to the polysulfide solution for a time and a temperature sufficient to form a precipitate in the solution;

(d) separating the precipitate from the solution to obtain a precipitate-free solution;

(e) contacting the precipitate-free solution with additional ammonium sulfide solution, containing from about 9 wt. % to about 13 wt. % sulfide sulfur, in an amount and for a time and at a temperature sufficient to form $(NH_4)_2Mo_2S_{12}.yH_2O$; and, (f) when X is to be other than $NH_4+$, the $(NH_4)_2Mo_2S_{12}.yH_2O$ formed in step (e) is separated, dried and then contacted with a solution of cation exchange compound containing a cation selected from group consisting of $Na+$, $K+$, $R_4N+$, $R_3NH+$, $R_2NH_2+$, $RNH_3+$, $R_4P+$, $R_4As+$, $(R_3P)_2N+$, where R is a $C_1$-$C_{30}$ alkyl, $C_6$-$C_{30}$ aryl, $C_7$-$C_{30}$ aralkyl or $C_2$-$C_{30}$ alkoxyalkyl group, and mixtures thereof, and an anion selected from the group consisting of $Cl-$, $Br-$, $F-$, $I-$, $BF_4-$, $PF_6-$, $OH-$, $Br_4-$, where R is a $C_1$-$C_{30}$ alkyl, $C_6$-$C_{30}$ aryl, $C_7$-$C_{30}$ aralkyl; $C_2$-$C_{30}$ alkoxyalkyl group, and mixtures thereof, and for a time sufficient to form a precipitate of the general formula $X_2Mo_2S_{12}.YH_2O$, where X is not $NH_4+$.

2. The method of claim 1 wherein step (a) comprises preparing a sulfide solution by obtaining and diluting a sulfide solution having 19 wt. % or greater sulfide sulfur with an appropriate amount of water until the sulfide solution has from about 9 wt. % to about 13 wt. % sulfide sulfur.

3. The method of claim 1 wherein the molybdenum compound is ammonium molybdate.

4. The method of claim 1 wherein the hydroxide is ammonium hydroxide.

5. The method of claim 1 wherein the time for step (c) ranges from about 1 hour to about 48 hours.

6. The method of claim 5 wherein said time is about 1 hour.

7. The method of claim 1 wherein the temperature ranges from about 0° C. to about 100° C.

8. The method of claim 7 wherein said temperature is room temperature (25° C.).

9. A method for preparing $(NH_4)_2Mo_2S_{12}.yH_2O$ where y is from 0 to 2, comprising:

(a) preparing an ammonium sulfide solution, containing from about 9 wt. % to about 13 wt. % sulfide sulfur;

(b) contacting the ammonium sulfide solution with elemental sulfur and ammonium hydroxide to form an ammonium polysulfide solution;

(c) adding ammonia molybdate to the polysulfide solution and stirring the combination for about 1 hour to about 24 hours at room temperature (25° C.) and atmospheric pressure to form a precipitate in the solution;

(d) separating the precipitate from the solution to obtain a precipitate free solution;

(e) contacting the precipitate free solution with an ammonium sulfide solution, containing from about 9 wt. % to about 13 wt. % sulfide sulfur, in an amount and for a time sufficient to form $(NH_4)_2Mo_2S_{12} \cdot yH_2O$.

* * * * *